United States Patent
Lui et al.

(10) Patent No.: US 8,273,904 B2
(45) Date of Patent: Sep. 25, 2012

(54) METHOD FOR PREPARING 4-AMINOBUT-2-ENOLIDES

(75) Inventors: Norbert Lui, Odenthal (DE); Jens-Dietmar Heinrich, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 167 days.

(21) Appl. No.: 12/677,769

(22) PCT Filed: Sep. 5, 2008

(86) PCT No.: PCT/EP2008/007270
§ 371 (c)(1),
(2), (4) Date: Mar. 11, 2010

(87) PCT Pub. No.: WO2009/036899
PCT Pub. Date: Mar. 26, 2009

(65) Prior Publication Data
US 2010/0190990 A1    Jul. 29, 2010

(30) Foreign Application Priority Data
Sep. 18, 2007 (EP) .................. 07116639

(51) Int. Cl.
*C07D 307/00* (2006.01)
*C07D 405/00* (2006.01)
(52) U.S. Cl. .............. 549/322; 549/321; 546/284.4
(58) Field of Classification Search ............ 549/322, 549/321; 546/284.4
See application file for complete search history.

(56) References Cited

FOREIGN PATENT DOCUMENTS

| | | |
|---|---|---|
| CH | 503 722 | 4/1971 |
| EP | 0 123 095 A2 | 10/1984 |
| EP | 0 153 615 A1 | 9/1985 |
| EP | 0 539 588 A1 | 5/1993 |
| WO | 2007/115643 A1 | 10/2007 |
| WO | 2007/115644 A1 | 10/2007 |
| WO | 2007/115646 A1 | 10/2007 |

OTHER PUBLICATIONS

Campbell et al. J.Chem.Soc. PerKin I 1985, 1567-1576.*
Mavrov et al. Russian Chemical Bulletin (2005), 54(12), 2857-2866.*
Haynes et al. Journal of the Chemical Society (1956) 4661-4 CAS No. 21053-90-7.*
Dorwald F. A. (Side Reactions in Organic Synthesis, 2005, Wiley: VCH, Weinheim p. IX of Preface p. 1-15.*
European Search Report based on PCT/EP2008/007270 dated Apr. 11, 2008.
Mitsos et al.; "Synthesis of Tetronic Acid Derivatives From Novel Active Esters of α-Hydroxyacids"; Journal of Heterocyclic Chemistry, 39(6), 1201-1205, 2002.
Athanasellis, et al.; "Novel Short-Step Synthesis of Optically Active Tetronic Acids From Chiral α-Hydroxy Acids Meditated by 1-Hydroxybenzotriazole"; Synlett, (10): 1736-1738, 2002.
Campbell et al; "Synthesis of (E)-and (Z)-Pulvinones"; Journal of the Chemical Society, Perkin Transaction 1, Chemical Society, Letchworth, GB, vol. 1, 1985, pp. 1567-1576.
International Search Report based on PCT/EP2008/007270 dated Jan. 5. 2009.

* cited by examiner

*Primary Examiner* — Nizal Chandrakumar
(74) *Attorney, Agent, or Firm* — Baker Donelson Bearman Caldwell & Berkowitz, PC

(57) ABSTRACT

Process for preparing 2,2-difluoroethylamine derivatives, wherein compounds of the general formula (IV) are reduced to the corresponding 2,2-difluoroethylamine derivatives of the general formula (III), where the A radical is as defined in the description:

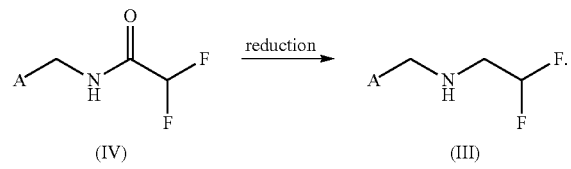

16 Claims, No Drawings

METHOD FOR PREPARING 4-AMINOBUT-2-ENOLIDES

CROSS REFERENCE TO RELATED APPLICATIONS

This application is a §371 National Stage Application of PCT/EP2008/007270 filed Sep. 5, 2008, which claims priority to European Application 07116639.1 filed Sep. 18, 2007.

BACKGROUND OF THE INVENTION

1. Field of the Invention

The present invention relates to a process for preparing 4-amino-but-2-enolides and corresponding intermediates or starting compounds which are passed through or used in the process according to the invention. The present invention further provides processes for preparing the intermediates and starting compounds in question.

2. Description of Related Art

Particular substituted 4-aminobut-2-enolide compounds are known as insecticidally active compounds from EP 0 539 588 A1. In addition, International Patent Applications WO 2007/115644, WO 2007/115643 and WO 2007/115646 describe corresponding insecticidally active 4-aminobut-2-enolide compounds.

In general, enaminocarbonyl compounds are synthesized from tetronic acid and an amine according to the following scheme 1. This procedure is described, for example, in EP 0 539 588 A1 and in Heterocycles Vol. 27, No. 8, pages 1907 to 1923 (1988).

Scheme 1:

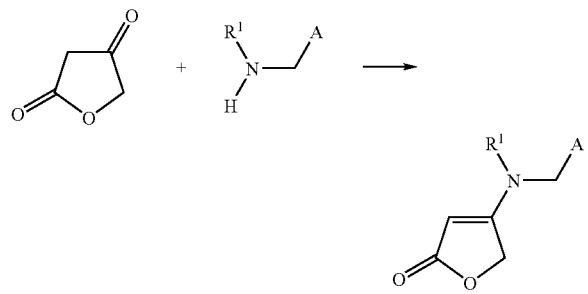

A disadvantage of this process is more particularly that anhydrous tetronic acid is required as a starting compound, the preparation of which is inconvenient and costly.

For instance, tetronic acid is generally prepared proceeding from ethyl acetoacetate via a bromination and subsequent hydrogenation (cf. Synthetic Communication, 11(5), pages 385 to 390 (1981)). The total yield of tetronic acid proceeding from ethyl acetoacetate is less than 40%, which makes the process relatively unattractive from an industrial point of view.

CH Patent 503 722 describes a further process for preparing tetronic acid. In this process, ethyl 4-chloroacetoacetate is reacted with an aromatic amine to give 3-arylaminocrotonolactone and then the tetronic acid is released by treatment with mineral acids. The disadvantage of this process is that the isolation of the tetronic acid is possible only by high-vacuum sublimation, which also makes this process relatively unattractive from an industrial point of view.

A further process for preparing tetronic acid is described in EP 0 153 615 A, in which the starting materials are 2,4-dichloroacetoacetic esters. This likewise multistage and complicated process likewise affords the desired compound only with a moderate overall yield of 65%.

Tetrahedron Letters, No. 31, pages 2683 and 2684 (1974) describes the preparation of tetronic acid and a corresponding enaminocarbonyl compound. The synthesis described there is reproduced in scheme 2 which follows. The reactant used is dimethyl acetylenedicarboxylate.

Scheme 2:

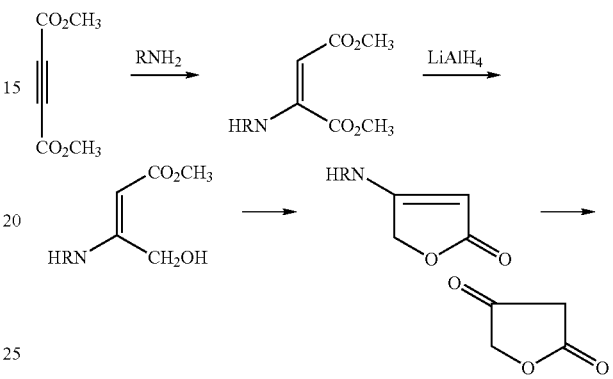

A disadvantage of this process is the low overall yield of only 30% and the requirement to have to use costly reactants, for example lithium aluminium hydride (LiAlH$_4$), as reagents.

Also disclosed in the prior art is a process for preparing 4-aminobut-2-enolides proceeding from methyl tetronate (J. Heterocyclic Chem., 21, 1753 (1984)). For this process, the starting material used is the costly 4-bromo-3-methoxybut-3-enecarboxylic ester.

A further process proceeds from a 4-chloroacetoacetic ester, which is reacted with amines (Heterocycles, Vol. 27, No. 8, 1988, pages 1907 to 1923). The reaction to give the aminofuran is carried out in one step. The amine is added with glacial acetic acid to a solution of 4-chloroacetoacetic ester in benzene and the resulting mixture is heated under reflux for several hours. The yields of 4-methylamino-2(5H)-furanone in this synthesis are only 40%.

EP 0 123 095 A discloses a process in which tetronamide is prepared from 3-amino-4-acetoxycrotonic ester. 3-Amino-4-acetoxycrotonic ester is costly and inconvenient to prepare, and so an economically viable synthesis with this process is not possible.

A further process for preparing tetronic acid proceeding from malonic esters and chloroacetyl chloride is known from J. Chem. Soc., Perkin Trans. 1 (1972), No. 9/10, pages 1225 to 1231. This process affords the desired target compound with a yield of only 43%.

The aforementioned International Patent Application WO 2007/115644 describes the preparation of 4-aminobut-2-enolides, for example of 4-[[(6-chloropyridin-3-yl)methyl](3,3-dichloroprop-2-en-1-yl)amino]furan-2(5H)-one by reaction of 4-[[(6-chloropyridin-3-yl)methyl]amino]furan-2(5H)-one with 3-bromo-1,1-dichloroprop-1-ene (cf. preparation example, process 2, Example (3)). WO 2007/115644 also describes the preparation of 4-aminobut-2-enolides, for example of 4-[[(6-chloropyridin-3-yl)methyl](3,3-dichloroprop-2-en-1-yl)amino]furan-2(5H)-one by reaction of 4-[[(2-fluoroethyl)amino]furan-2(5H)-one with 2-chloro-5-chloromethylpyridine (cf. preparation examples, process 3, Example (4)). The reactions are preferably carried out with hydrides of lithium or of sodium. These substrates are generally costly and can simultaneously be handled only with difficulty for safety reasons.

SUMMARY OF THE INVENTION

Proceeding from this prior art, it is an object of the present invention to provide a process for preparing 4-aminobut-2-enolide compounds which is preferably simple and inexpensive to perform. The 4-aminobut-2-enolide compounds obtainable by this desired process should preferably be obtained with high yield and high purity. More particularly, the process desired should enable the desired target compounds to be obtained without the necessity of complex purification methods.

This object is achieved by a process for preparing 4-aminobut-2-enolide compounds of the general formula (I):

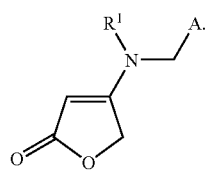
(I)

The process according to the invention is characterized in that compounds of the general formula (II)

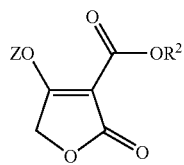
(II)

are reacted with amines of the general formula (III)

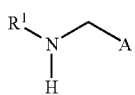
(III)

where the individual radicals are defined as follows:
$R^1$ is hydrogen, alkyl, haloalkyl, alkenyl, haloalkenyl, alkynyl, cycloalkyl, cycloalkylalkyl, halocycloalkyl, alkoxy, alkyoxyalkyl, halocycloalkylalkyl or arylalkyl;
$R^2$ is alkyl, aryl or arylalkyl;
Z is hydrogen, an alkali metal or alkaline earth metal;
A is pyrid-2-yl or pyrid-4-yl, or is pyrid-3-yl which is optionally 6-substituted by fluorine, chlorine, bromine, methyl, trifluoromethyl or trifluoromethoxy, or is pyridazin-3-yl which is optionally 6-substituted by chlorine or methyl, or is pyrazin-3-yl or is 2-chloropyrazin-5-yl or is 1,3-thiazol-5-yl which is optionally 2-substituted by chlorine or methyl, or
pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, $C_1$-$C_4$-alkyl (which is optionally substituted by fluorine and/or chlorine), $C_1$-$C_3$-allylthio (which is optionally substituted by fluorine and/or chlorine), or $C_1$-$C_3$-alkylsulphonyl (which is optionally substituted by fluorine and/or chlorine), or

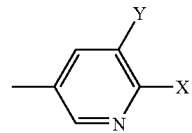

in which
X is halogen, alkyl or haloalkyl and
Y is halogen, alkyl, haloalkyl, haloalkoxy, azido or cyano.

DETAILED DESCRIPTION OF A PREFERRED EMBODIMENT

The invention thus provides that the desired 4-aminobut-2-enolide compounds of the general formula (I) are prepared by a reaction of the corresponding tetronic esters of the general formula (II) with amines of the general formula (III). The desired 4-aminobut-2-enolide compounds of the general formula (I) are obtained under the inventive reaction conditions and preferred reaction conditions which are specified in detail below with good yields and in high purity, as a result of which the process according to the invention overcomes the abovementioned disadvantages of the prior art processes. The desired compounds are obtained in a purity which generally does not necessitate a comprehensive workup of the direct reaction products.

Preferred, particularly preferred and very particularly preferred definitions of the A radical shown in the abovementioned general formulae (I) and (III) are elucidated below.

A is preferably selected from the group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

A is more preferably selected from the group consisting of 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.

A is most preferably selected from the group consisting of 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.

Preferred, particularly preferred and very particularly preferred definitions of the Z, $R^1$ and $R^2$ radicals shown in the abovementioned general formula (II) are elucidated below.

Z is preferably selected from the group consisting of alkali metals and hydrogen;

Z is more preferably selected from the group consisting of hydrogen, sodium and potassium;

Z is most preferably sodium or hydrogen;

$R^1$ is preferably selected from hydrogen, alkyl, haloalkyl, alkenyl, haloalkenyl, alkynyl, cycloalkyl, cycloalkylalkyl, halocycloalkyl, halocycloalkylalkyl and alkoxyalkyl.

$R^2$ is more preferably selected from the group consisting of methyl, ethyl, propyl, vinyl, allyl, propargyl, cyclopropyl, alkoxyalkyl, 2-fluoroethyl, 2,2-difluoroethyl and 2-fluorocyclopropyl.

$R^1$ is most preferably selected from the group consisting of methyl, ethyl, n-propyl, n-prop-2-enyl, n-prop-2-ynyl, cyclopropyl, methoxyethyl, 2-fluoroethyl and 2,2-difluoroethyl.

$R^2$ is preferably selected from the group consisting of $C_1$-$C_{12}$-alkyl, $C_6$-aryl and aralkyl.

$R^2$ is more preferably selected from the group consisting of $C_1$-$C_{12}$-alkyl.

$R^2$ is most preferably selected from the group consisting of methyl and ethyl.

In a preferred embodiment of the present invention, starting compounds of the general formulae (II) and (III) in which the substituents A, Z, $R^1$ and $R^2$ each have the aforementioned preferred definitions are used in the process according to the invention.

In a particularly preferred embodiment of the present invention, starting compounds of the general formulae (II) and (III) in which the substituents A, Z, $R^1$ and $R^2$ each have the aforementioned particularly preferred definitions are used in the process according to the invention.

In a very particularly preferred embodiment of the present invention, starting compounds of the general formulae (II) and (III) in which the substituents A, Z, $R^1$ and $R^2$ each have the aforementioned very particularly preferred definitions are used in the process according to the invention.

In the context of the invention—irrespective of the abovementioned preferred, particularly preferred and very particularly preferred individual definitions—the following definition is generally assigned to the radicals used in the individual case:

In the context of the present invention, the term "alkyl", either alone or else in combination with further terms, for example haloalkyl, alkoxyalkyl, cycloalkylalkyl, halocycloalkylalkyl and arylalkyl, is understood to mean a radical of a saturated, aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, $C_1$-$C_6$-alkyl radicals are particularly preferred. Especially preferred are $C_1$-$C_4$-alkyl radicals, especially methyl and ethyl.

According to the invention, the term "alkenyl" is understood to mean a linear or branched $C_1$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hex-enyl, 5-hexenyl and 1,4-hexadienyl. Among these, preference is given to $C_2$-$C_6$-alkenyl radicals and particular preference to $C_1$-$C_4$-alkenyl radicals.

According to the invention, the term "alkynyl" is understood to mean a linear or branched $C_3$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also have at least one double bond.

According to the invention, the term "cycloalkyl" is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

According to the invention, the term "aryl" is understood to mean an aromatic radical having 6 to 14 carbon atoms, preferably phenyl.

The term "arylalkyl" is understood to mean a combination of "aryl" and "alkyl" radicals defined in accordance with the invention, where the radical is generally bonded via the alkyl group; examples thereof are benzyl, phenylethyl or α-methylbenzyl, particular preference being given to benzyl.

In the context of the present invention, halogen-substituted radicals, for example haloalkyl, are understood to mean radicals halogenated once or more than once up to the maximum possible number of substituents. In the case of polyhalogenation, the halogen atoms may be the same or different. Halogen is fluorine, chlorine, bromine or iodine, especially fluorine, chlorine or bromine.

The term "alkoxy", either alone or else in combination with further terms, for example haloalkoxy, is understood in the present context to mean an O-alkyl radical, the term "alkyl" being as defined above.

Optionally substituted radicals may be substituted once or more than once, and the substituents may be the same or different in the case of polysubstitution.

The compounds of the general formula (II) may be present in different tautomeric forms:

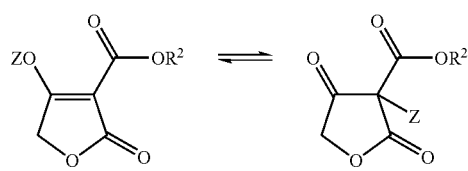

Especially when Z is hydrogen, the compounds are present in different forms owing to keto-enol tautomerism. In the context of the present invention—irrespective of the way in which the compound of the formula (II) is represented, all tautomeric structures of the general formula (II) are encompassed.

The compounds of the general formula are at least partly known from the prior art. For example, the following compounds of the general formula (II) where Z is hydrogen or potassium and $R^2$ is ethyl and the preparation of these compounds are described in J. Chem. Soc., Perkin Trans. 1, 1985, pages 1567 to 1576:

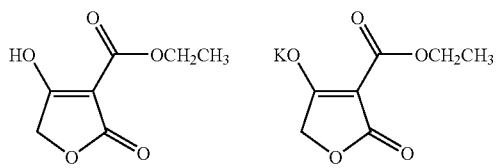
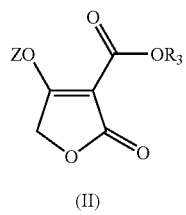

The synthesis of correspondingly modified derivatives of the compounds of the general formula (II) can be carried out according to scheme 3 below, for example proceeding from potassium salts of the malonic esters of the general formula (IV) via the compound of the general formula (V) using alkoxide bases, such as sodium methoxide $NaOCH_3$ where $R^2=CH_3$ and $Z=Na$:

Scheme 3:

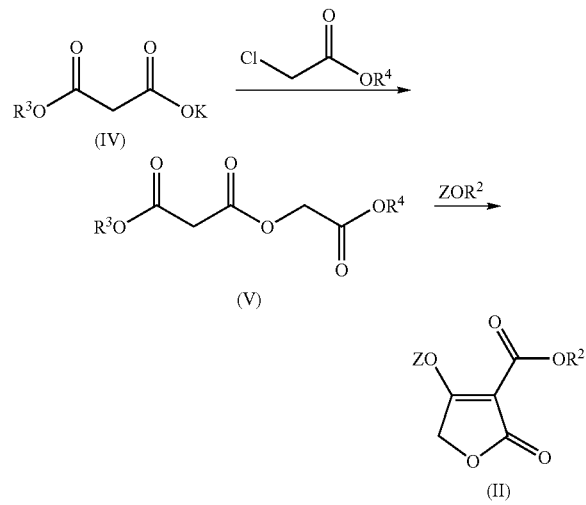

Depending on the steric size of the alkoxide radical, there may, as in the case of the sodium alkoxide in scheme 3, be an exchange of the ester radical (in scheme 3, the ester radical in the compound of the general formula (V) is exchanged for $R^2$). When, however, a sterically more demanding radical is selected, the ester exchange can be reduced or even suppressed.

When, for example, potassium tert-butoxide is used as the base in this synthesis, there is no exchange of the substituent $R^3$, which thus remains in the target compound (scheme 4).

Scheme 4:

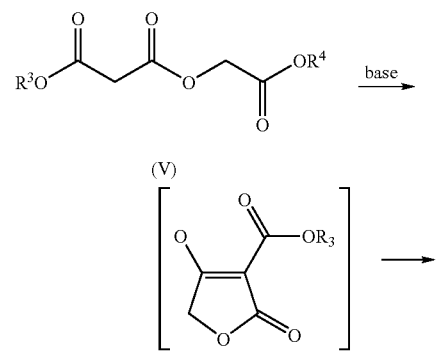

In addition, the compounds of the general formula (II) where Z=hydrogen are prepared proceeding from malonic ester and chloroacetyl chloride according to the following scheme 5 as per the prior art Berichte der Deutschen Chemischen Gesellschaft (1911), 44, 1759-1765 (in the compound of the general form (II), the keto form is shown, i.e. Z is hydrogen):

Scheme 5:

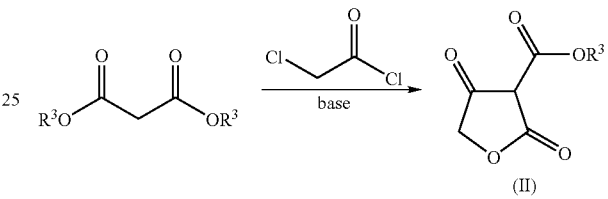

In this scheme, the individual radicals, if present, are generally defined as follows:
$R^2$ is as defined above;
$R^3$ is alkyl, with the exception of ethyl, cycloalkyl, haloalkyl, aryl or arylalkyl;
$R^4$ is alkyl, cycloalkyl, haloalkyl, aryl or arylalkyl; and
Z is as defined above.

The potassium salts of the malonic esters of the general formula (IV) used as reactants are commercially available or can be prepared by processes known from the prior art (cf. J. Am. Chem. Soc., 1944, No. 66, page 1286).

The prior art discloses neither the sodium salts (Z=Na) or corresponding methyl esters ($R^2=CH_3$) of the general formula (II), which therefore, as intermediates of the inventive synthesis—as described below—form a further part of the subject-matter of the present invention.

More particularly, the use of the corresponding sodium salts of the general formula (II) (X=Na) is preferred in the process according to the invention, since the sodium salts—in contrast to the potassium salts known from the prior art—can be synthesized inexpensively owing to the replacement of the potassium tert-butoxide base with sodium methoxide.

The present invention further provides, in addition—as likewise described below—the process described above in scheme 3 for preparing the corresponding sodium salts (Z=Na) and/or methyl esters ($R^2=CH_3$) of the general formula (II) according to the scheme shown above.

The amines of the general formula (III) required for the inventive reaction are commercially available or can be prepared by processes known from the literature (cf., for example, S. Patai "The Chemistry of Amino Group". Interscience Publishers, New York, 1968).

The reaction of the ester compounds of the general formula (II) with the amines of the general formula (III) can be carried out in the presence of solvents (diluents). Solvents are advantageously) used in such an amount that the reaction mixture remains readily stirrable over the entire process. Useful solvents for performing the process according to the invention include all organic solvents which are inert under the reaction conditions.

Examples include: halohydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; ethers, such as ethyl propyl ether, methyl tert-butyl ether, methyl n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether; methyl-THF and polyethers of ethylene oxide and/or propylene oxide; nitrohydrocarbons such as nitromethane, nitroethane, nitropropane, nitrobenzene, chloronitrobenzene, o-nitrotoluene; nitriles such as acetonitrile, methyl nitrile, propionitrile, butyronitrile, isobutyronitrile, benzonitrile, phenyl nitrile, m-chlorobenzonitrile, and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons such as pentane, n-hexane, n-heptane, n-octane, nonane, for example white spirits with components having boiling points in the range, for example, of 40° C. to 250° C. cymene, petroleum fractions within a boiling range of 70° C. to 190° C., cyclohexane, methylcyclohexane, petroleum ether, ligroin, octane, benzene, toluene, xylene; esters such as methyl, ethyl, butyl and isobutyl acetate, and also dimethyl, dibutyl and ethylene carbonate; amides such as hexamethylenephosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; and aliphatic alcohols such as methanol, ethanol, n-propanol and isopropanol and n-butanol.

The inventive reaction is preferably carried out in a solvent which is selected from the group consisting of dioxane, butyronitrile, propionitrile, acetonitrile, DME, toluene, methyl-THF, dichlorobenzene, chlorobenzene, n-heptane, isobutanol, n-butanol, ethanol, methyl tert-butyl ether, isopropyl ethyl ether and mixtures thereof.

In some cases, depending on the exact starting compounds, it is also possible to conduct the reaction in bulk, i.e. without addition of solvents.

The reaction of the compounds of the general formula (II) with the amines of the general formula (III) is preferably conducted in the presence of a Brønsted acid.

It is possible to use either organic or inorganic acids. Preference is given to using inorganic acids, for example phosphoric acid ($H_3PO_4$), sulphuric acid ($H_2SO_4$), hydrochloric acid (HCl), hydrobromic acid (HBr), hydrofluoric acid (HF) or potassium hydrogensulphate ($KHSO_4$). The individual acids may be used either in anhydrous form or in hydrous form, for example in the form of 85% phosphoric acid or 37% hydrochloric acid, i.e. more particularly in forms in which the acids are commercially available. Examples of suitable organic acids are trifluoroacetic acid, acetic acid, methanesulphonic acid and p-toluenesulphonic acid. Among the aforementioned acids, preference is given especially to phosphoric acid, sulphuric acid, potassium hydrogensulphate and trifluoroacetic acid.

The reaction to prepare the compounds of the general formula (I) can be conducted generally under reduced pressure, at standard pressure or under elevated pressure. The temperatures employed may likewise vary depending on the substrates used and are easy for the person skilled in the art to determine by routine tests. For example, the reaction to prepare the compounds of the general formula (I) can be conducted at a temperature of 20 to 200° C., preferably 20 to 150° C. Particular preference is given to conducting the reaction at temperatures of 20 to 150° C.

The stoichiometry of the starting compounds of the general formula (II) and (III) used may vary within wide ranges and is generally not subject to any particular restriction. Suitable stoichiometries of the starting compounds of the general formula (II) and (III) used can be determined easily by the person skilled in the art by routine tests. For instance, the molar ratio of the compound of the general formula (II) to the amine of the general formula (III) used may, for example, be 0.5 to 10, in particular 1 to 6, especially 1.05 to 2. The use of greater amounts of compound of the general formula (III) is possible in principle, but does not lead to a preferred embodiment and is disadvantageous for economic reasons.

Towards the end of the reaction, the water of reaction can be removed as an azeotrope by distilling a portion of the solvent. In the case of high-boiling solvents, this can be done under reduced pressure. By virtue of this operation, a quantitative conversion is generally achieved.

If the reaction is conducted in a solvent, the solvent can be removed by distilling it off after the end of the reaction. This can be done under standard pressure or reduced pressure at room temperature or at elevated temperatures.

The desired compounds of the general formula (I) can also be isolated, for example, by crystallization.

As already mentioned, some of the compounds of the general formula (II) are not known from the prior art. These novel compounds used as starting compounds for the process according to the invention form a further part of the subject-matter of the present invention.

In a first further embodiment, the present invention therefore also relates to compounds of the general formula (IIa)

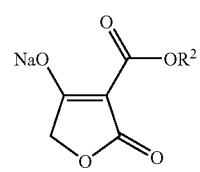

(IIa)

in which $R^2$ is as defined above.

The compounds of the general formula (IIa) are present in the form of sodium salts.

In a second further embodiment, the present invention further relates to compounds of the general formula (IIb)

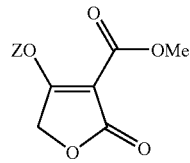
(IIb)

in which
is selected from the group consisting of alkali metals and alkaline earth metals.

The compounds of the general formula (II), especially the compounds of the formula (IIa) and (IIb), are obtained proceeding from the compounds of the general formula (IV) by cyclization.

For the cyclization itself, it is possible to use any desired base, for example potassium tert-butoxide or sodium methoxide, though preference is given to sodium methoxide for economic reasons.

Suitable solvents for the cyclization reaction are, for example, those which are also used for the inventive preparation of the 4-amino-but-2-enolide compounds of the general formula (I).

The cyclization can generally be carried out under reduced pressure, at standard pressure or under elevated pressure. The temperatures employed may likewise vary depending on the substrates used and are easy for the person skilled in the art to determine by routine tests. For example, the reaction to prepare the compounds of the general formula (V) can be conducted at a temperature of 20 to 200° C., preferably 20 to 150° C. Particular preference is given to performing the reaction at standard pressure and temperatures of 20 to 150° C.

The stoichiometry of the starting compounds of the general formula (V) used relative to the base used may vary within wide ranges and is generally not subject to any particular restriction. Suitable stoichiometries of the starting compounds of the general formula (V) used and of the base can be determined by the person skilled in the art easily by routine tests. For instance, the molar ratio of the compound of the general formula (V) to the base may, for example, be 0.9 to 10, in particular 1 to 5, especially 1 to 2.

The compounds of the general formula (V) can in turn be prepared by reacting the known or commercially available potassium salts of the malonic esters with alkyl haloacetates. In general, it is possible to use alkyl bromoacetates, especially ethyl bromoacetate, and alkyl chloroacetates, especially ethyl chloroacetate. The appropriate chlorine derivatives are particularly preferred, since the corresponding bromine derivatives are more expensive.

The present invention therefore also relates to the preparation of the compounds of the general formula (V)

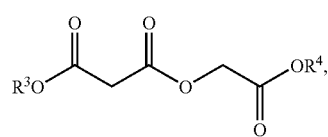
(V)

characterized in that compounds of the general formula (IV)

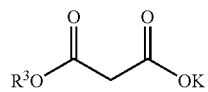
(IV)

are reacted with alkyl chloroacetates, especially ethyl chloroacetate, of the general formula (VI)

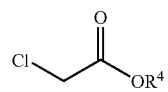
(VI)

where
the individual substituents $R^3$ and $R^4$ are each as defined above.

These reactions to give the compounds of the general formula (V) are typically conducted in a solvent.

Suitable solvents are, for example, those which are also used for the inventive preparation of the 4-aminobut-2-enolide compounds of the general formula (I). Particular preference is given among these to dimethylformamide and dimethylacetamide.

The reaction to prepare the compounds of the general formula (V) can generally be conducted under reduced pressure, at standard pressure or under elevated pressure. The temperatures employed may likewise vary depending on the substrates used and are easy for the person skilled in the art to determine by routine tests. For example, the reaction to prepare the compounds of the general formula (V) can be conducted at a temperature of 20 to 200° C., preferably 20 to 150° C. Particular preference is given to performing the reaction at standard pressure and temperatures of 20 to 150° C.

The stoichiometry of the starting compounds of the general formula (IV) and (VI) used may vary within wide ranges and is generally not subject to any particular restriction. Suitable stoichiometries of the starting compounds of the general formula (IV) and (VI) used can be determined easily by the person skilled in the art by routine tests. For instance, the molar ratio of the compound of the general formula (IV) to the ester of the general formula (VI) used may, for example, be 5 to 0.8, in particular 3 to 0.9, especially 2 to 1.

If the reaction is carried out in a solvent, the solvent can be removed by distilling it off after the end of the reaction. This can be done under standard pressure or reduced pressure, at room temperature or elevated temperatures.

The desired compounds of the general formula (V) can also be isolated, for example, by crystallization.

Furthermore, it is also possible to convert the compounds of the general formula (V) directly, i.e. more particularly without purification, to the compounds of the general formula (II).

The present invention is illustrated in detail by the examples which follow, though the examples should not be interpreted in such a way that they restrict the invention.

PREPARATION EXAMPLES

Example 1

To a suspension of 10.4 g of potassium 4-(ethoxycarbonyl)-5-oxo-2,5-dihydrofuran-3-oxide and 7.5 g of N-[(6- chloropyridin-3-yl)methyl]-2,2-difluoroethylamine in 68 ml of butyronitrile are added, at room temperature, 11.5 g of potassium hydrogensulphate. The mixture is stirred at a temperature of 90 to 95° C. for 3 hours. Subsequently, the mixture is cooled to room temperature, 120 ml of water and 120 ml of dichloromethane are added, the organic phase is removed and the aqueous phase is extracted twice with 120 ml each time of methylene chloride. The combined organic phases are concentrated to dryness. 11.4 g of 4-[[(6-chloropyridin-3-yl)methyl](2,2-difluoroethyl)amino]furan-2(5H)-one are obtained in a purity of 84% (this corresponds to 92% yield).

Example 2

To a suspension of 5 g of sodium 4-(methoxycarbonyl)-5-oxo-2,5-dihydrofuran-3-oxide and 4.2 g of N-[(6-chloropyridin-3-yl)methyl]-2,2-difluoroethylamine in 35 ml of butyronitrile are added, at room temperature, 7.5 g of potassium hydrogensulphate. The mixture is stirred at a temperature of 90° C. for 3 hours. Subsequently, the mixture is cooled to room temperature and admixed with 60 ml of water and 60 ml of dichloromethane. The organic phase is removed and the aqueous phase is extracted twice with 30 ml each time of methylene chloride. The combined organic phases are concentrated to dryness. 5.95 g of 4-[[(6-chloropyridin-3-yl)methyl](2,2-difluoroethyl)amino]furan-2(5H)-one are obtained in a purity of 89% (this corresponds to 91% yield).

Example 3

To a suspension of 10 g of sodium 4-(methoxycarbonyl)-5-oxo-2,5-dihydrofuran-3-oxide and sodium 4-(ethoxycarbonyl)-5-oxo-2,5-dihydrofuran-3-oxide (ratio 77:23) and 3.5 g of N-[(6-chloropyridin-3-yl)methyl]methylamine in 35 ml of butyronitrile are added, at room temperature, 7.5 g of potassium hydrogensulphate. The mixture is stirred at a temperature of 90° C. for 3 hours. Subsequently, the mixture is cooled to room temperature and the solvent is removed completely. The residue is admixed with 50 ml of water and extracted twice with 30 ml each time of dichloromethane. The combined organic phases are concentrated to dryness. 4.7 g of 4-[[(6-chloropyridin-3-yl)methyl]methylamino]furan-2(5H)-one are obtained in a purity of 95% (this corresponds to 82% yield).

Example 4

To a suspension of 78.9 g of potassium monoethylmalonate in 500 ml of dimethylformamide are added dropwise, at 35° C., 55 g of methyl chloroacetate and the mixture is stirred at 35° C. for 8 hours. The solvent is removed under reduced pressure and the residue is admixed with 100 ml of water and 100 ml of toluene. The phases are separated and the aqueous phase is washed with 100 ml of toluene. The combined organic phases are dried over magnesium sulphate and concentrated under reduced pressure. 77.6 g of methyl 2-methoxy-2-oxoethylpropanedicarboxylate are obtained in a purity of 98% (this corresponds to 80% yield).
$^1$H NMR (CDCl$_3$, 298 K) δ: 3.51 s (2H), 3.77 s (3H), 3.78 s (3H), 4.69 s (2H)

Example 5

To 19.6 g of methyl 2-methoxy-2-oxoethylpropanedicarboxylate are added dropwise, at 40° C., 18 g of 30% sodium methoxide in methanol, and the mixture is heated under reflux for 3 hours. Subsequently, the mixture is cooled to room temperature, and the solids are filtered off with suction and washed with 20 ml of methanol. The product is dried at 50° C. under reduced pressure. 15.6 g of sodium 4-(methoxycarbonyl)-5-oxo-2,5-dihydrofuran-3-oxide are obtained in a purity of 99.9% (this corresponds to 87% yield).
$^1$H NMR (D$_2$O, 298 K) δ: 3.73 s (3H), 4.42 s (2H)

Example 6

To 23.1 g of ethyl 2-ethoxy-2-oxoethylpropanedicarboxylate are added dropwise, at 40° C., 18 g of 30% sodium methoxide in methanol, and the mixture is heated under reflux for 2 hours. Subsequently, the mixture is cooled to 0° C., and the solids are filtered off with suction and washed with 10 ml of methanol. The product is dried at 50° C. under reduced pressure. A mixture of 15.7 g of sodium 4-(methoxycarbonyl)-5-oxo-2,5-dihydrofuran-3-oxide and sodium 4-(ethoxycarbonyl)-5-oxo-2,5-dihydrofuran-3-oxide (ratio 77:23) is obtained (this corresponds to 86% yield).

Example 7

To a suspension of 5.2 g of 4-(methoxycarbonyl)-5-oxo-2,5-dihydrofuran-3-ol and 5 g of N-[(6-chloropyridin-3-yl)methyl]-2,2-difluoroethylamine in 70 ml of butyronitrile are added, at room temperature. 4.5 g of potassium hydrogensulphate. The mixture is stirred at a temperature of 120° C. for 3 hours. Subsequently, the mixture is cooled to room temperature and admixed with 60 ml of water and 60 ml of dichloromethane. The organic phase is removed and the aqueous phase is extracted twice with 30 ml each time of methylene chloride. The combined organic phases are concentrated to dryness. 7.6 g of 4-[[(6-chloropyridin-3-yl)methyl](2,2-difluoroethyl)amino]furan-2(5H)-one are obtained in a purity of 85% (this corresponds to 94% yield).

Example 8

To a suspension of 18 g of 4-(methoxycarbonyl)-5-oxo-2,5-dihydrofuran-3-ol and 15 g of N-[(6-chloropyridin-3-yl)methyl]methylamine in 210 ml of butyronitrile are added, at room temperature, 16 g of potassium hydrogensulphate. The mixture is stirred at a temperature of 115° C. for 5 hours. Subsequently, the mixture is cooled to room temperature and admixed with 150 ml of water and 70 ml of dichloromethane. The organic phase is removed and the aqueous phase is extracted twice with 70 ml each time of methylene chloride. The combined organic phases are concentrated to dryness. 24 g of 4-[[(6-chloropyridin-3-yl)methyl](methyl)amino]furan-2(5H)-one are obtained in a purity of 88% (this corresponds to 92% yield).

The invention claimed is:
1. A process for preparing a 4-aminobut-2-enolide compound of formula (I)

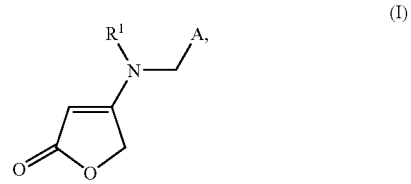

comprising reacting a compound of formula (II)

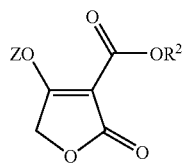

with an amine of formula (III)

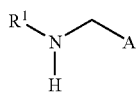

where
R¹ is hydrogen, alkyl, fluoroalkyl, alkenyl, fluoroalkenyl, alkynyl, cycloalkyl, cycloalkylalkyl, fluorocycloalkyl, alkoxy, alkoxyalkyl, fluorocycloalkylalkyl or arylalkyl;
R² is alkyl, aryl or arylalkyl;
Z is hydrogen, an alkali metal or an alkaline earth metal;
A is pyrid-2-yl or pyrid-4-yl, or is pyrid-3-yl which is optionally 6-substituted by fluorine, chlorine, bromine, methyl, trifluoromethyl or trifluoromethoxy, or is

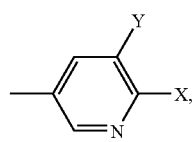

in which
X is halogen, alkyl or fluoroalkyl, and
Y is halogen, alkyl, fluoroalkyl, or fluoroalkoxy.

2. The process according to claim 1, wherein the compound of the formula (II) is obtained by reacting a compound of formula (V)

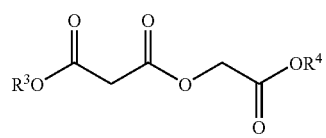

wherein
R³ alkyl, with the exception of ethyl, or cycloalkyl; and
R⁴ is alkyl, cycloalkyl, fluoroalkyl, aryl or arylalkyl with a base.

3. The process according to claim 2, wherein the compound of formula (II) is obtained by the following scheme proceeding from a compound of formula (V) by reaction with sodium alkoxide:

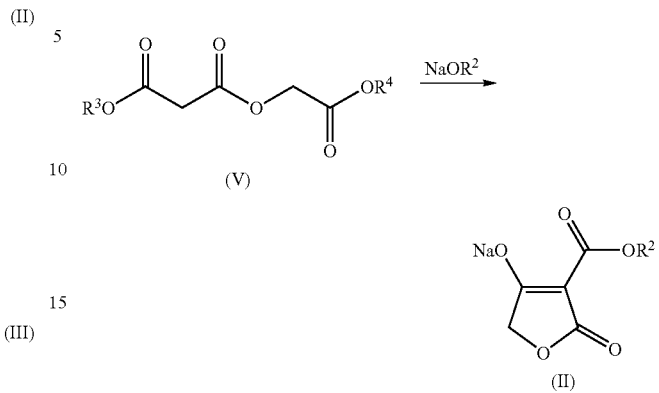

where
R² is alkyl, aryl or arylalkyl;
R³ is alkyl, with the exception of ethyl, or cycloalkyl; and
R⁴ is alkyl, cycloalkyl, fluoroalkyl, aryl or arylalkyl.

4. The process according to claim 2, wherein the compound of formula (II) is obtained by the following scheme proceeding from a compound of formula (V) by reaction with potassium tert-butoxide:

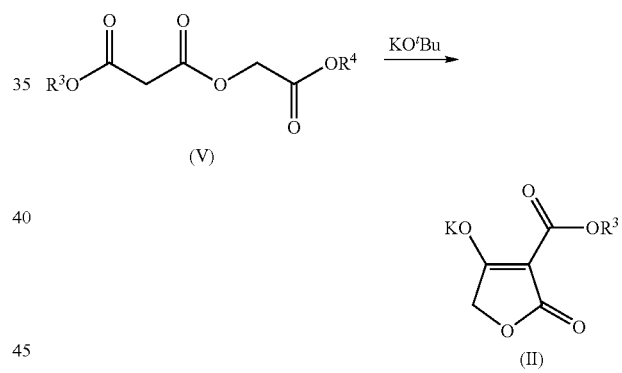

where
R³ is alkyl, with the exception of ethyl, or cycloalkyl; and
R⁴ is alkyl, cycloalkyl, fluoroalkyl, aryl or arylalkyl.

5. The process according to claim 1, wherein the compound of formula (II) is obtained by the following scheme proceeding from malonic esters and chloroacetyl chloride:

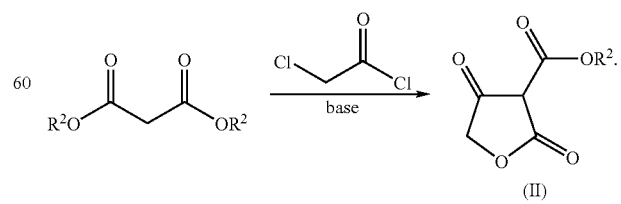

where R² is alkyl, aryl or arylalkyl.

6. A process for preparing a compound of formula (V)

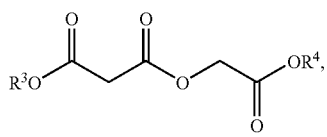

comprising reacting a compound of formula (IV)

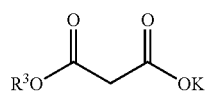

with an alkyl chloro acetate of formula (VI)

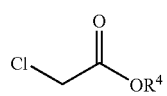

where
R$^3$ is alkyl, with the exception of ethyl, or cycloalkyl;
R$^4$ is alkyl, cycloalkyl, fluoroalkyl, aryl or arylalkyl.

7. The process according to claim 1, wherein A is

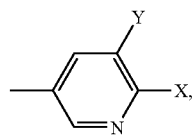

in which
X is halogen, alkyl or fluoroalkyl, and
Y is halogen, alkyl, fluoroalkyl, or fluoroalkoxy.

8. The process according to claim 7, wherein A is

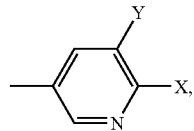

in which
X is halogen, alkyl or fluoroalkyl and
Y is halogen, alkyl, fluoroalkyl, fluoroalkoxy, azido or cyano.

9. The process according to claim 1, wherein
R$^1$ is hydrogen, alkyl, fluoroalkyl, alkenyl, fluoroalkenyl, alkynyl, cycloalkyl, cycloalkylalkyl, fluorocycloalkyl, fluorocycloalkylalkyl, or alkoxyalkyl,
R$^2$ is C$_1$-C$_{12}$-alkyl, C$_6$-aryl, or aralkyl, and
Z is an alkali metal or hydrogen.

10. The process according to claim 1, wherein
R$^1$ is methyl, ethyl, propyl, vinyl, allyl, propargyl, cyclopropyl, alkoxyalkyl, 2 fluoroethyl, 2,2-difluoroethyl, or 2-fluorocyclopropyl, and
R$^2$ is C$_1$-C$_{12}$-alkyl, and
Z is hydrogen, sodium, or potassium.

11. The process according to claim 1, wherein
R$^1$ is methyl, ethyl, n-propyl, n-prop-2-enyl, n-prop-2-ynyl, cyclopropyl, methoxyethyl, 2-fluoroethyl, or 2,2-difluoroethyl, and
R$^2$ is methyl or ethyl, and
Z is sodium or hydrogen.

12. The process according to claim 1, wherein
A is pyrid-2-yl, which is optionally 6-substituted by fluorine, chlorine, bromine, methyl, trifluoromethyl, or trifluoromethoxy.

13. The process according to claim 1, wherein
A is pyrid-3-yl, which is optionally 6-substituted by fluorine, chlorine, bromine, methyl, trifluoromethyl, or trifluoromethoxy.

14. The process according to claim 1, wherein
A is pyrid-4-yl, which is optionally 6-substituted by fluorine, chlorine, bromine, methyl, trifluoromethyl, or trifluoromethoxy.

15. The process according to claim 2, wherein the base is alkoxide.

16. The process according to claim 6, wherein the alkyl chloroacetate is ethyl chloroacetate.

* * * * *